(12) United States Patent
Palumbo et al.

(10) Patent No.: US 6,491,673 B1
(45) Date of Patent: Dec. 10, 2002

(54) DISPOSABLE URINE COLLECTOR

(75) Inventors: Gianfranco Palumbo, Bad Homburg (DE); Vincenzo D'Acchioli, Kelkheim/Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,183

(22) PCT Filed: Jun. 26, 1998

(86) PCT No.: PCT/US98/13289
§ 371 (c)(1),
(2), (4) Date: Mar. 7, 2001

(87) PCT Pub. No.: WO00/00113
PCT Pub. Date: Jan. 6, 2000

(51) Int. Cl.[7] .................................................. A61F 13/15
(52) U.S. Cl. ........................ 604/317; 604/327; 604/355; 604/358
(58) Field of Search ..................... 2/400–406, 247–250; 604/317–402

(56) References Cited

U.S. PATENT DOCUMENTS

| | | | | |
|---|---|---|---|---|
| 3,532,093 A | * | 10/1970 | Lovret | 604/347 |
| 3,577,989 A | * | 5/1971 | Anderson | 604/347 |
| 4,553,969 A | * | 11/1985 | Taylor | 604/355 |
| 4,834,737 A | * | 5/1989 | Khan | 604/385.2 |
| 6,007,524 A | * | 12/1999 | Schneider | 604/327 |

* cited by examiner

Primary Examiner—Jeanette Chapman
(74) Attorney, Agent, or Firm—Ian S. Robinson; Matthew P. Fitzpatrick; Len W. Lewis

(57) ABSTRACT

A disposable urine management device including a bag having an aperture which is surrounded by an adhesively-faced flange for releasable attachment to the uro-genital area of the wearer. An absorbent material is contained within the bag.

11 Claims, 6 Drawing Sheets

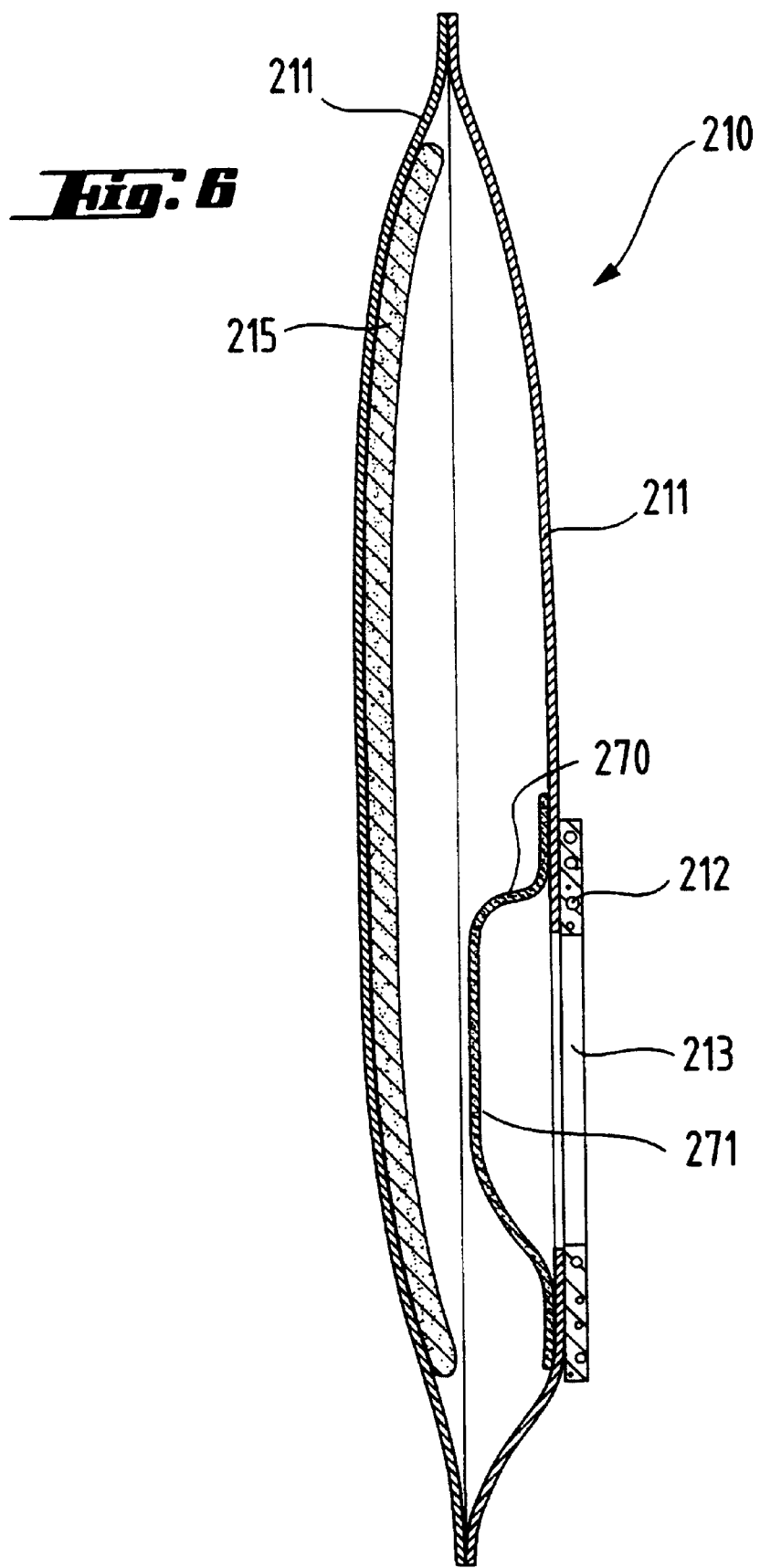

DISPOSABLE URINE COLLECTOR

FIELD OF THE INVENTION

This invention relates to disposable urine management devices, and more particularly, to disposable urine management devices with improved fit and conformability.

BACKGROUND OF THE INVENTION

Disposable urine management devices in the form of urine incontinence protection devices or in the form of urine collection devices for medical purposes are known in the art.

Representative devices of the former type are disclosed in EP 0 140 470 and WO 85/0328, both of which disclose disposable devices which include a water-impervious barrier sheet formed as a bag, an opening to be located next to the wearer's uro-genital area to receive the discharged urine, and containing an absorbent material to absorb the discharged urine. EP 0 140 470 additionally discloses the presence of a wicking layer between the opening and the absorbent material. Neither of these references disclose the use of an adhesive member or flange surrounding the aperture for securing the bag to the body of the wearer.

Representative of the urine collector art is U.S. Pat. No. 4,804,377 which discloses a urine collector device for infants or small children having a flexible collection bag and an adhesively-faced attachment member joined to the bag. The urine collectors in general by definition do not contain any absorbent material as they are designed to collect urine; they must be of sufficient dimension to contain a full discharge, and are therefore, bulky. Furthermore, they are not designed to be worn for any length of time next to the body, or to be worn inside an undergarment or diaper.

It is now been found that a superior disposable urine management device can be designed, which ensures perfect fit and conformability to the wearer, and is designed to be worn in lieu of a diaper by a baby, small child or incontinent adult.

BRIEF SUMMARY OF THE INVENTION

The invention is a disposable urine management device. The disposable urine management device comprises a bag having an aperture which is surrounded by an adhesively-faced flange for releasable attachment to the uro-genital area of the wearer. An absorbent material is contained within said bag.

BRIEF DESCRIPTION OF THE DRAWINGS

While the Specification concludes with claims pointing out and distinctly claiming the present invention, it is believed the same will be better understood by the following drawings taken in conjunction with the accompanying Specification wherein like components are given the same reference number.

FIG. 6 is a cross-sectional view of another embodiment of a disposable urine management device of the present invention.

DETAILED DESCRIPTION OF THE INVENTION

The term "disposable" as used herein describes devices which generally are not intended to be laundered or otherwise restored or reused (i.e., they are intended to be discarded after a single use and, preferably, to be recycled, composted or otherwise disposed of in an environmentally compatible manner.)

Figure 1:
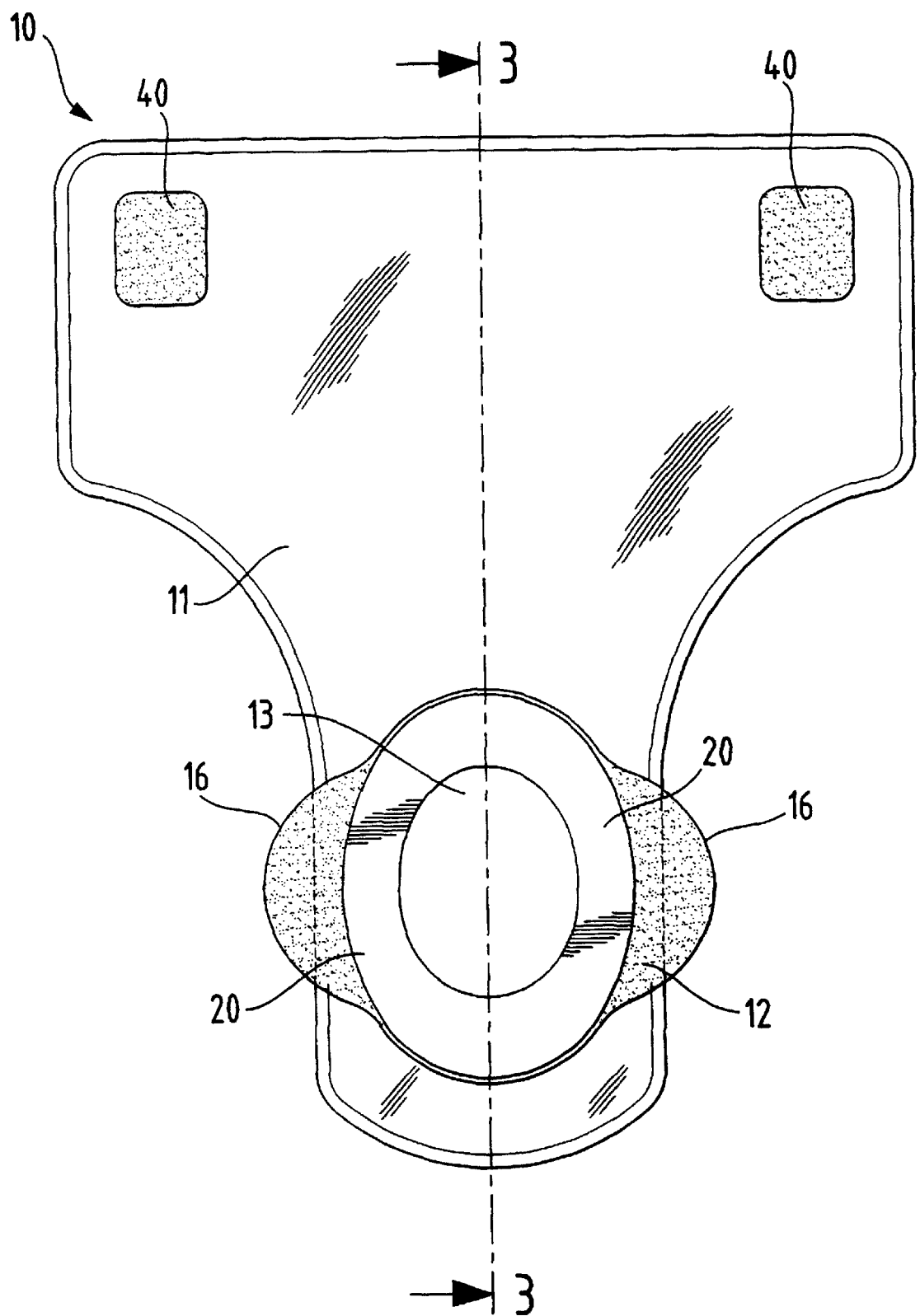
FIG. 1 is a plan view of a disposable urine management device of the present invention.
Figure 2:
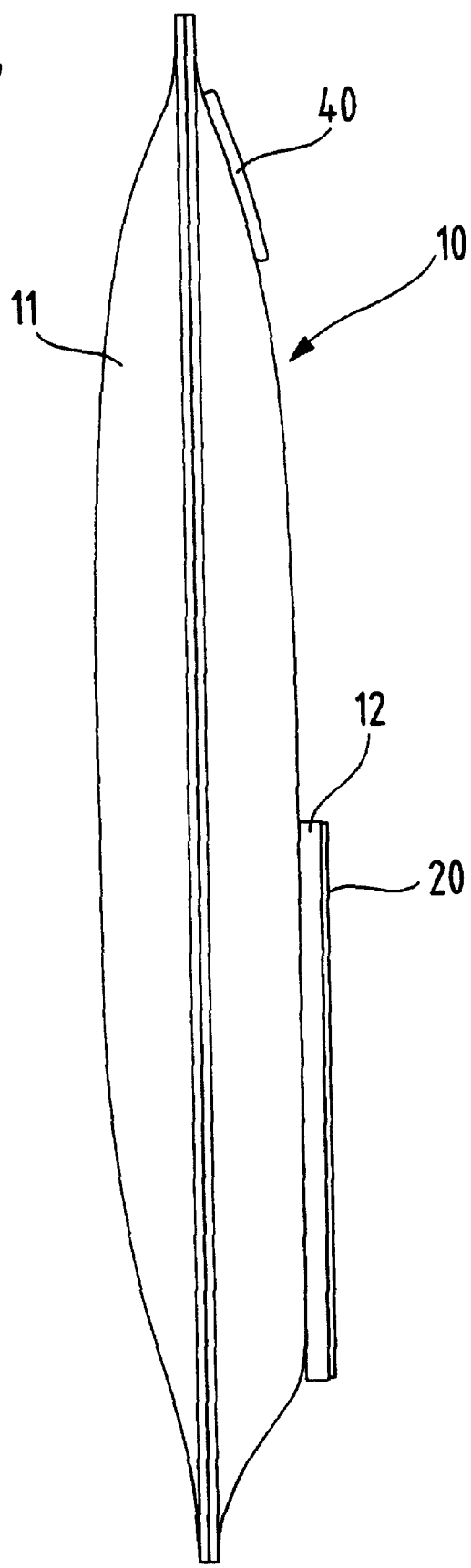
FIG. 2 is a side view of the disposable urine management device of FIG. 1.
Figure 3:
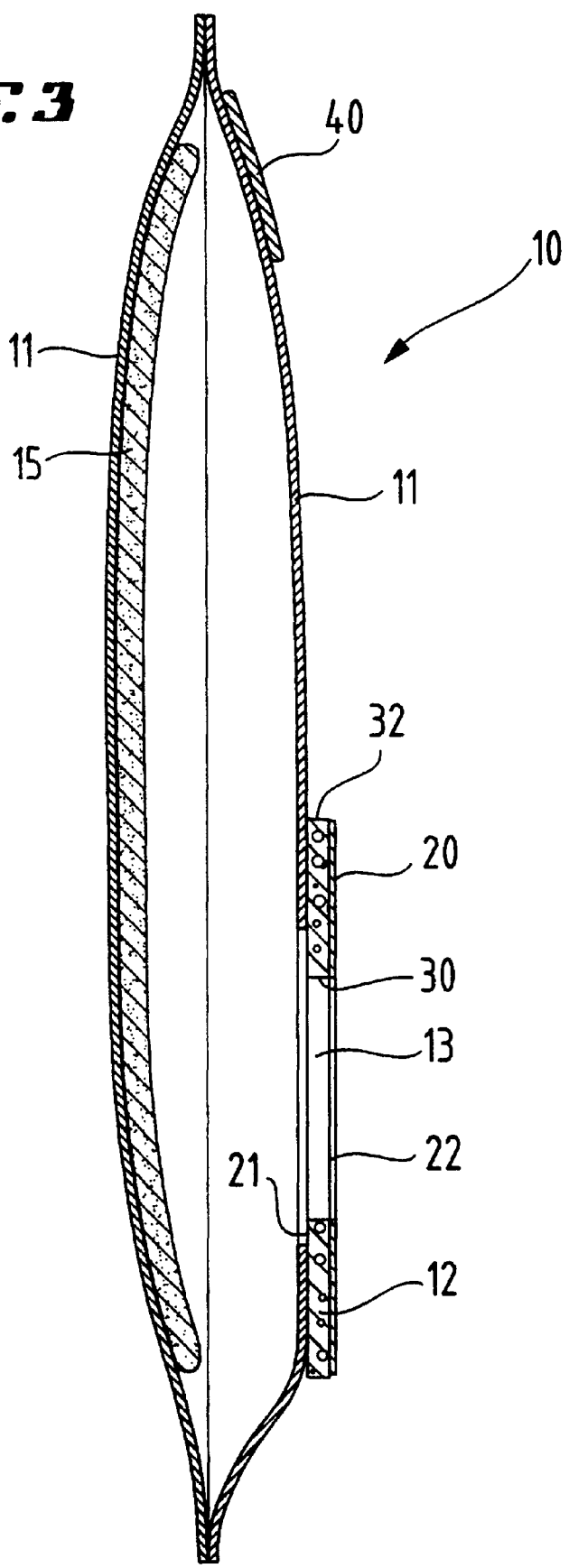
FIG. 3 is a cross-sectional view taken along line 3—3 of FIG. 1.

Referring now to FIGS. 1–3, there is shown a disposable urine management device (10). Disposable urine management device (10) comprises a bag (11) having an aperture (13) and a flange (12) surrounding the aperture for adhesive attachment to the body of a wearer.

The bag (11) as used herein is a flexible receptacle for the containment of discharged urine. The bag (11) can be provided in any shape or size depending on the intended use thereof, i.e. whether the device is intended for bedridden patients or active patients suffering from incontinence. For example elongated bags which are principally tubular or rectangular are typically utilized by bedridden patients and elderly incontinence sufferers. For more active wearers whether infants or adults, the urine management device should preferably be anatomically shaped such that the device follows the contours of the body and can be worn inconspicuously by the wearer under normal garments.

Particularly, preferred shapes are cone shaped bags, truncated shaped bags and pyramidal or truncated pyramidal or cone shaped bags. In a most preferred embodiment of the present invention, the bag (11) has a substantially truncated cone shape.

In addition, the bag (11) is preferably shaped to fit the uro-genital region of the wearer to ensure good contact between the flange (12) and the skin of the wearer.

The bag (11) is preferably designed to provide sufficient volume for urine under a variety of wearing conditions, also when worn by a freely moving, i.e., not bedridden wearer.

The bag (11) is designed to safely contain any entrapped material, typically it will be liquid impermeable, yet it may be breathable. The bag is designed of sufficient strength to resist rupturing in use.

According to the present invention, depending on the shape of the bag (11) required, the bag may be made from a unitary piece of material or from a number of separate pieces of material, which may be identical or different and which are sealed at their respective peripheries.

According to the present invention the bag can comprise one or multiple layers, preferably two or three layers. The layer on the inside of the bag, which will typically at least partially come in contact with urine is called the inner layer. The outermost layer of the bag, which will typically at least partially come in contact with the skin of the wearer and the garments of the wearer, is called the outer layer.

The layers of the bag material may be provided from any material, so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fiberglass, rayon, polyester, polyolefin, acrylic, polyamid. aramid, polytetrafluroethylene metal, polyimide; binders such as bicomponent high melt/low melt polymer, copolymer polyester, polyvinyl chloride, polyvinyl acetate/ chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film.

In yet another preferred embodiment of the present invention, the bag (11) comprises three layers, preferably one film layer and two non-woven layers. In an even more preferred embodiment the film is interposed between the two non-woven layers. This sequence of layers results in a closed fibrous structure, which has a particularly pleasing sensation on contact with the skin of the wearer.

The non-woven layer or the non-woven layers comprised by the bag (11) may be hydrophobic or hydrophilic. For example, if the bag comprises a film layer, further non-woven layers may be hydrophilic or hydrophobic. If the bag does not comprise a film layer, preferably at least one non-woven layer is hydrophobic. It may even be desirable to make both non-woven layers hydrophobic to ensure that the bag is liquid impervious.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness. The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

As shown in FIG. 1 the bag (11) is provided with an aperture (13) whereby urine is received from the body prior to storage within the bag cavity. The aperture (13) is surrounded by a flange (12) and may be provided in any shape or size, such as circular, oblong, heart shaped and may be symmetrical or asymmetrical, preferably the aperture has an oblong configuration either in the longitudinal or in the transversal direction, most preferably the contours of the aperture are in the shape of two ellipses with the respective main axes being substantially perpendicular.

The flange (12) is attached to the bag (11) according to means known to the man skilled in the art, preferably adhesives.

The flange may be provided in any size depending on the wearer group for which the device is intended. Similarly the flange may be provided in any shape and preferably has a symmetrical, slightly oblong shape, preferably comprising a plurality of lobes.

The flange comprises a wearer facing surface (22) and an opposed garment facing surface (21). In a preferred embodiment these are two large, substantially flat surfaces.

The flange (12) should be made of soft, flexible and malleable material to allow easy placement of the flange to the uro-genital area. In addition, it is preferred that the flange (12) be made of a hydrophobic material such that if urine does come into contact with the perimeter (30) surrounding aperture (13) it is repelled and does not wick to the outer edge (32) of flange (12). It is also desirable to construct the flange (12) from a breathable material to avoid the problem of entrapment and condensation of moisture vapour given off by the body of the wearer and thus, the hot, clammy and uncomfortable conditions after a short period of use.

Suitable materials for the flange (12) include but are not limited to non-woven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

According to the present invention the wearer facing surface (22) of the flange (12) comprises a body-compatible adhesive (20). The adhesive (20) is preferably covered with a release means (not shown) in order to protect the adhesive layer prior to use, such as siliconized paper. The adhesive (20) can cover the entire wearer facing surface of the flange or more preferably have at least one, preferably two to six non-adhesive portions. These portions may be adhesive free or may contain inactivated or covered adhesives. As is evident from FIG. 1, the adhesive (20) is in one preferred embodiment not applied to the entire wearer facing surface area of the flange (12), so as to provide lobes (16) on either side of the flange (12) which are non-adhesive and can thereby serve as placement lobes to facilitate placement and removal of the device whilst avoiding contact with the adhesive. These lobes are however preferably also covered by the release paper. Before application of the urine management device (10) to the skin of the wearer, the release means if present is removed.

According to the present invention any medically approved water resistant pressure sensitive adhesive may be used to attach the device to the uro-genital area of the wearer, such as hydrocolloid adhesives and hydrogel adhesives. Particularly effective adhesives in providing the desired adhesive properties to secure the flange to the skin of the wearer at the sensitive uro-genital area, whilst allowing for relatively painless application and removal are hydrophillic hydrogels formed from crosslinking polymers with a plastisicer to form a 3-dimensional matrix.

The adhesive (20) can be applied to the wearer facing surface (22) of the flange (12) by any means known in the art such as slot coating, spiral, or bead application or printing. Typically the adhesive is applied at a basis weight of from 20 g/m² to 2500 g/m², more preferably from 500 g/m² to 2000 g/m² most preferably from 700 g/m² to 1500 g/m² depending on the end use envisioned. For example for urine management devices to be used for children the amount of adhesive may be less than for urine management devices designed for active adult incontinence sufferers.

Absorbent material (15) is contained within the bag (11). The absorbent material (15) may comprise any absorbent material which is capable of absorbing and retaining liquids such as urine. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or crosslinked cellulosic fibers; tissue, including tissue wraps and tissue laminates; absorbent foams; absorbent sponges; superabsorbent polymers; absorbent gelling materials; or any other known absorbent material or combinations of materials.

The absorbent material (15) may be positioned in the bag (11) in any suitable manner. For example, the absorbent material (15) may be loosely arranged within the bag (15) or may be secured to the inner layer of the bag (11). Any known techniques for securing absorbent material to non-woven and film substrates may be used to secure the absorbent material (15) to the inner layer of the bag. The absorbent material may also be arranged to have any desired shape or configuration (e.g., rectangular, oval, circular, etc.).

In the embodiment shown in FIGS. 1—3, the outer surface of bag (11) is provided with patches of adhesive (40) for securing the bag (11) to the body of the wearer. Preferably, the patches of adhesive (40) are positioned on the outer surface of bag (11) such that they are secured to the abdomen of the wearer in use. Any number, size and shape of adhesive patches (40) may be used depending on the intended use of the device. The adhesive (40) may be any medically approved water resistant pressure sensitive adhesive such as hydrocolloid adhesives and hydrogel adhesives. Particularly effective adhesives in providing the desired adhesive properties to secure the flange to the skin of the wearer whilst allowing for relatively painless application and removal are hydrophillic hydrogels formed from crosslinking polymers with a plastisicer to form a 3-dimensional matrix.

Figure 4:
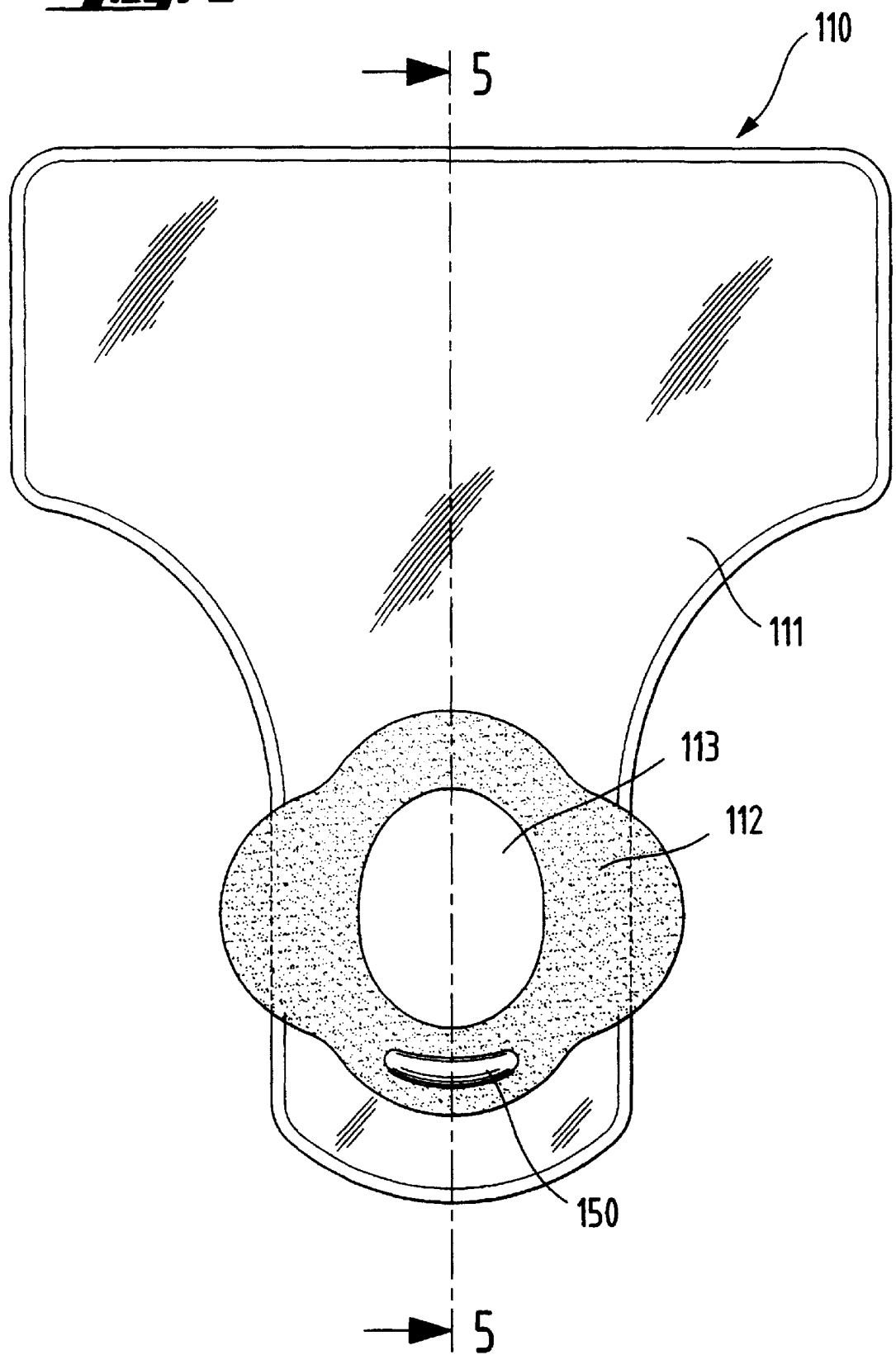
FIG. 4 is a plan view of another embodiment of a disposable urine management device of the present invention.
Figure 5:
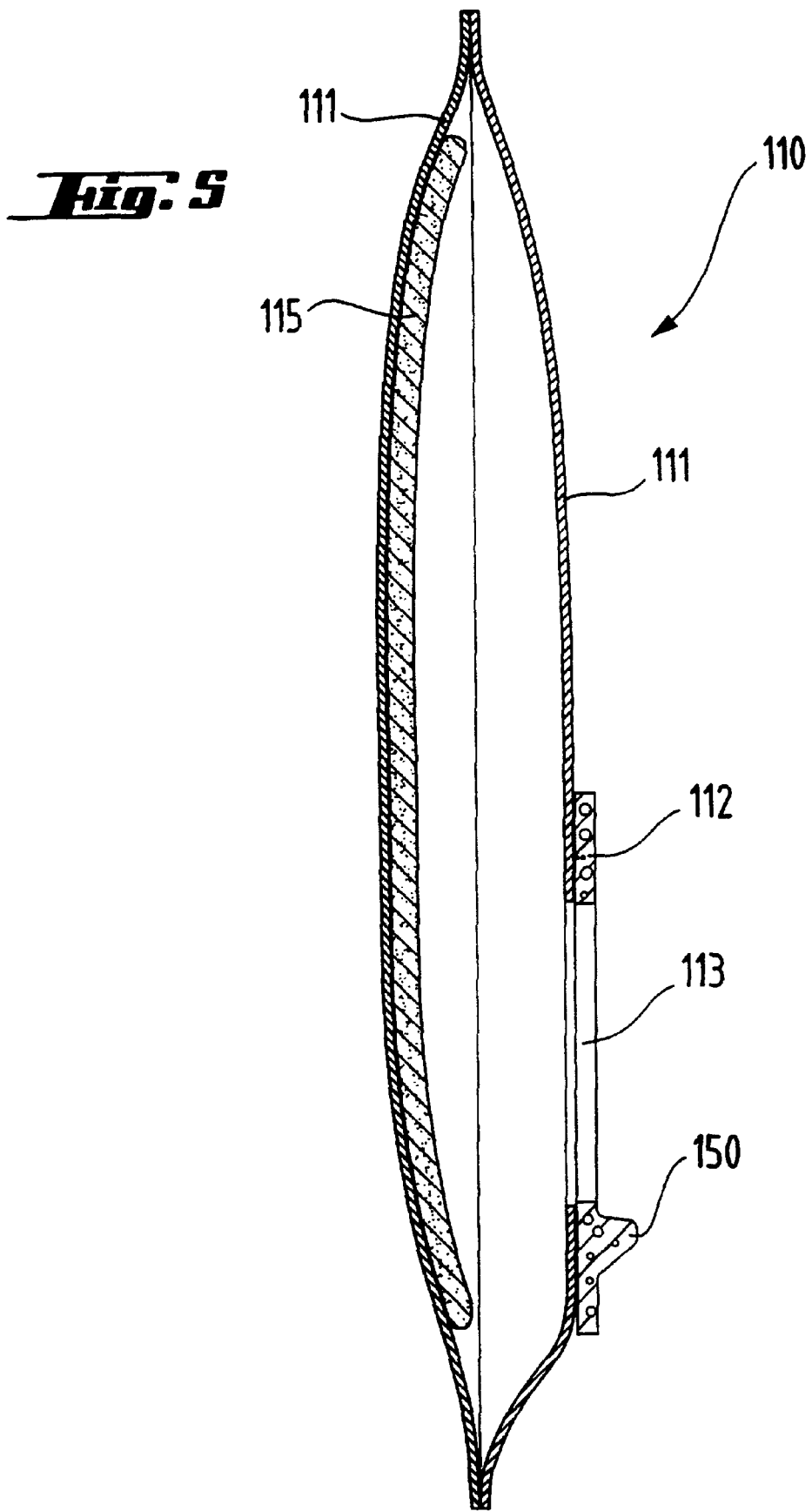
FIG. 5 is a cross-sectional view taken along line 5—5 of FIG. 4.

Referring now to FIGS. 4–5, there is shown another embodiment of a disposable urine management device (110). Disposable urine management device (110) comprises a bag (111) having an aperture (113), a flange (112) surrounding the aperture for adhesive attachment to the body of a wearer, and absorbent material (115) contained within the bag (111).

The flange (112) includes a raised, curved bulge (150) positioned beneath the aperture (113) and extending across the flange (112) for approximately the width of the aperture (113). The bulge (150) is shaped to span the perineum of an infant.

Referring now to FIG. 6, there is shown another embodiment of a disposable urine management device (210). Disposable urine management device (210) comprises a bag (211) having an aperture (213), a flange (212) surrounding the aperture for adhesive attachment to the body of a wearer, and absorbent material (215) contained within the bag (211).

Disposable urine management device (210) also comprises an additional acquisition layer (270). Acquisition layer (270) is shown in FIG. 6 to be secured to the inner surface of bag (211). However, the acquisition layer (270) may also be secured to the flange (212), or both the flange (212) and the inner surface of bag (211). Acquisition layer (270) is preferably positioned such that it separates the genitalia of the wearer from coming into direct contact with the absorbent material (215). Acquisition layer (270) is fluid pervious allowing urine to readily pass through so that it may be absorbed by absorbent material (215).

The acquisition layer (270) may be manufactured from a wide range of materials, such as porous foams; reticulated foams; apertured plastic films; or woven or non-woven webs of natural fibers (e.g., wood or cotton fibers), synthetic fibers (e.g., polyester or polypropylene fibers), or a combination of natural and synthetic fibers. If the acquisition, barrier layer includes fibers, the fibers may be spunbond, carded, wetlaid, meltblown, hydroentangled, or otherwise processed as is known in the art.

The acquisition layer (270) is designed to have a pore size such that the absorbent material (215) is not allowed to pass through and contact the wearer's skin. While designed not to have to large of a pore size which permits the passage of absorbent material (215), the acquisition layer (270) preferably has a pore size which is greater than the pore size of the absorbent material (215).

Preferably. the acquisition layer (270) is less hydrophilic than the absorbent material (215). The acquisition layer (270) may be treated with a surfactant to increase its initial wettability. When treated with surfactant, however, the acquisition layer (270) should still be less hydrophilic than the absorbent material (215). Suitable methods for treating the acquisition layer (270) with a surfactant include spraying the acquisition layer (270) with the surfactant and immersing the material into the surfactant. Alternatively, a surfactant may be incorporated into the acquisition layer (270).

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable urine management device (10) comprising a bag (11), wherein the bag comprises at least an inside layer, an outside layer and an aperture (13), said aperture being surrounded by an adhesively-faced flange (12) for releasable attachment to the uro-genital area of the wearer, characterized in that an absorbent material (15) is contained within said bag.

2. The disposable urine management device of claim 1 wherein said bag is liquid impermeable.

3. The disposable urine management device of claim 1 wherein said bag is breathable.

4. The disposable urine management device of claim 1 wherein said bag comprises at least one layer.

5. The disposable urine management device of claim 1 wherein said outside layer comprises a non-woven layer.

6. The disposable urine management device of claim 5 wherein said non-woven layer is impregnated with a lotion.

7. The disposable urine management device of claim 5 wherein said non-woven layer is hydrophobic.

8. The disposable urine management device of claim 1 wherein said absorbent material is selected from the group consisting of comminuted wood pulp; creped cellulose wadding; meltblown polymers; chemically stiffened, modified or cross-linked cellulosic fibers; tissue; absorbent foams; absorbent sponges; superabsorbent polymers; and absorbent gelling materials.

9. The disposable urine management device of claim 1 wherein said bag further comprises at least one adhesive patch (40).

10. The disposable urine management device of claim 1 wherein said flange further comprises a raised, curved bulge (150).

11. The disposable urine management device of claim 1 wherein said bag further comprises an acquisitionr layer (270).

* * * * *